(12) United States Patent
Judson

(10) Patent No.: US 6,944,767 B1
(45) Date of Patent: Sep. 13, 2005

(54) METHODS AND APPARATUS FOR ENSURING THE PRIVACY AND SECURITY OF PERSONAL MEDICAL INFORMATION

(75) Inventor: Richard S. Judson, Guilford, CT (US)

(73) Assignee: Genaissance Pharmaceuticals, Inc., New Haven, CT (US)

( * ) Notice: Subject to any disclaimer, the term of this patent is extended or adjusted under 35 U.S.C. 154(b) by 966 days.

(21) Appl. No.: 09/611,654

(22) Filed: Jul. 7, 2000

(51) Int. Cl.[7] .................................. H04L 9/00
(52) U.S. Cl. ........................ 713/185; 705/3; 705/5
(58) Field of Search ................ 705/3, 5, 2; 713/185

(56) References Cited

U.S. PATENT DOCUMENTS

| | | | |
|---|---|---|---|
| 3,970,996 A | 7/1976 | Yasaka et al. | |
| 4,491,725 A | 1/1985 | Pritchard | |
| 4,632,428 A | 12/1986 | Brown | |
| 4,896,027 A | 1/1990 | Drexler | |
| 5,193,541 A | 3/1993 | Hatsuwi | |
| 5,215,334 A | 6/1993 | Presson et al. | |
| 5,325,294 A * | 6/1994 | Keene | 705/3 |
| 5,499,293 A * | 3/1996 | Behram et al. | 705/76 |
| 5,612,870 A | 3/1997 | Welner | |
| 5,651,067 A | 7/1997 | Ahrens et al. | |
| 5,876,926 A | 3/1999 | Beecham | |
| 6,056,193 A * | 5/2000 | McAuliffe et al. | 235/380 |
| 6,081,793 A * | 6/2000 | Challener et al. | 705/50 |
| 6,523,116 B1 * | 2/2003 | Berman | 713/182 |

FOREIGN PATENT DOCUMENTS

| | | |
|---|---|---|
| WO | WO88/02700 | 4/1988 |

* cited by examiner

*Primary Examiner*—Gregory Morse
*Assistant Examiner*—Jacob Lipman
(74) *Attorney, Agent, or Firm*—Melodie Henderson; Sandra Shaner

(57) ABSTRACT

A method of ensuring the security of data from a medical test includes providing the patient with a medical data card issued by a secure information provider, and having a unique patient identification number (PID), a public key encryption private key, and public key encryption public key (Key 2). The method further includes a first test request card having an encrypted identification of the patient and the test, a health care provider code, Key 2, and the test type that accompanies the patient's test specimen to the secure information provider, a second test request card bearing an encryption of the PID and the test type to forward with the patient's specimen to a testing laboratory; a first test results card bearing an encryption of the PID and the results; and a second test results card that may be read in conjunction with the patient's medical data card.

9 Claims, 5 Drawing Sheets

METHODS AND APPARATUS FOR ENSURING THE PRIVACY AND SECURITY OF PERSONAL MEDICAL INFORMATION

FIELD OF THE INVENTION

This invention relates to methods and devices for ensuring the privacy and security of personal medical information, and in particular to methods and devices for ensuring the privacy and security of personal genetic information.

BACKGROUND OF THE INVENTION

As knowledge of the human genome increases, an increasing number of genetic markers are being identified as either the cause of, or being associated with, an increased risk of developing various diseases and conditions. Genetic testing for these markers will allow physicians to identify those at risk of developing certain diseases and take action to prevent, or at least reduce the risk of developing, these disease. It is also possible to test for genetic markers associated with variations in drug response, and to predict how a patient will respond to a particular drug treatment. However, despite the obvious medical benefit, people may be hesitant to permit such testing for fear that they might be discriminated against by prospective employers and insurers due to an increased risk of disease revealed by such a test, or an indication that a patient is not responsive to conventional treatment revealed by such a test. Thus, ensuring the privacy and security of medical information, and particularly genetic testing information, is important to encourage the public to permit such testing.

Some efforts have been made to provide anonymity for medical test results. For example, in the past numbered test kits have been available with which a person can take a sample, such as a blood sample, and mail the sample to the issuing laboratory, and anonymously call in for the test results by referencing the number on the test kit. However in many instances such a patient-initiated testing system is not appropriate, for example where it is not apparent to the patient what type of test to order, where the collection of the sample is not routine or within the ability of the patient, or where the significance of, or interpretation of, the results is not within the ability of patient. This is particularly true for testing for efficacy of certain courses of drug therapy. In these instances, a patient needs the assistance of a health care professional, and may avoid valuable tests out of concern for the privacy and security of the test results.

SUMMARY OF THE INVENTION

Generally, the method of this invention allows for the private and secure reporting of a patient's medical tests. The method comprises providing the patient with a medical data card (MDC) issued by a secure information provider (e.g., a trusted third party between the patient's physician or healthcare provider and a testing laboratory), and having a unique patient identification number (PID), a public key encryption private key (Key 1), and a public key encryption public key (Key 2). This medical data card may also include provision for storing information about medical tests conducted on the patient, including information about the type of test conducted, a unique identification number for the test, and the results of the test. The patient's medical data card is used to generate a first test request card (REQ1) that accompanies the test specimen taken from the patient to the secure information provider. The first test request card includes an encrypted identification of the patient and the test; a code identifying the health care provider; the patient identification number (PID); public encryption public key (Key 2); and an identification of the test type. The secure information provider uses the first test request card to generate a second test request card (REQ2) to forward the patient's specimen to a testing laboratory. The second test request card and the specimen are forwarded to the laboratory. The second test request card bears an encryption of the patent's unique identification number, but does not otherwise bear any indicia that would identify the patient. The specimen is sent to a laboratory, which performs the tests prescribed by the heath care professional, and generates a first test results card (RES1). The results, together with the patient's unique identification number, are provided to the secure information provider that issued the medical data card. The secure information provider encodes the test results onto a second test results card, and forwards the card to the health care provider. The health care provider can identify the patient from the information on the second test results card (RES2), and contact the patient. The test results on the second test results card can only be read in conjunction with the patient's medical data card. In the preferred embodiment, after reading the results, the results are transferred to the patient's medical data card.

The method and apparatus of the present invention thus allow for the private and secure reporting of medical test results, such as genetic test results. The specimen taken for the testing cannot be identified with a particular patient, during transmission to the laboratory, conduct of the testing, or reporting of the results. The results are provided to a secure information provider, who encodes the information on a test results card that can only be read in conjunction with the patient's medical data card. Even the secure information provider can operate without knowing the actual identity of the patient; although in some embodiments, the secure information provider may have access to both patient identity information and to the test results. Thus, the patient controls who has access to the testing information.

BRIEF DESCRIPTION OF THE DRAWINGS

Corresponding reference numerals indicate corresponding parts throughout the drawings.

DETAILED DESCRIPTION OF THE INVENTION

Figure 1:
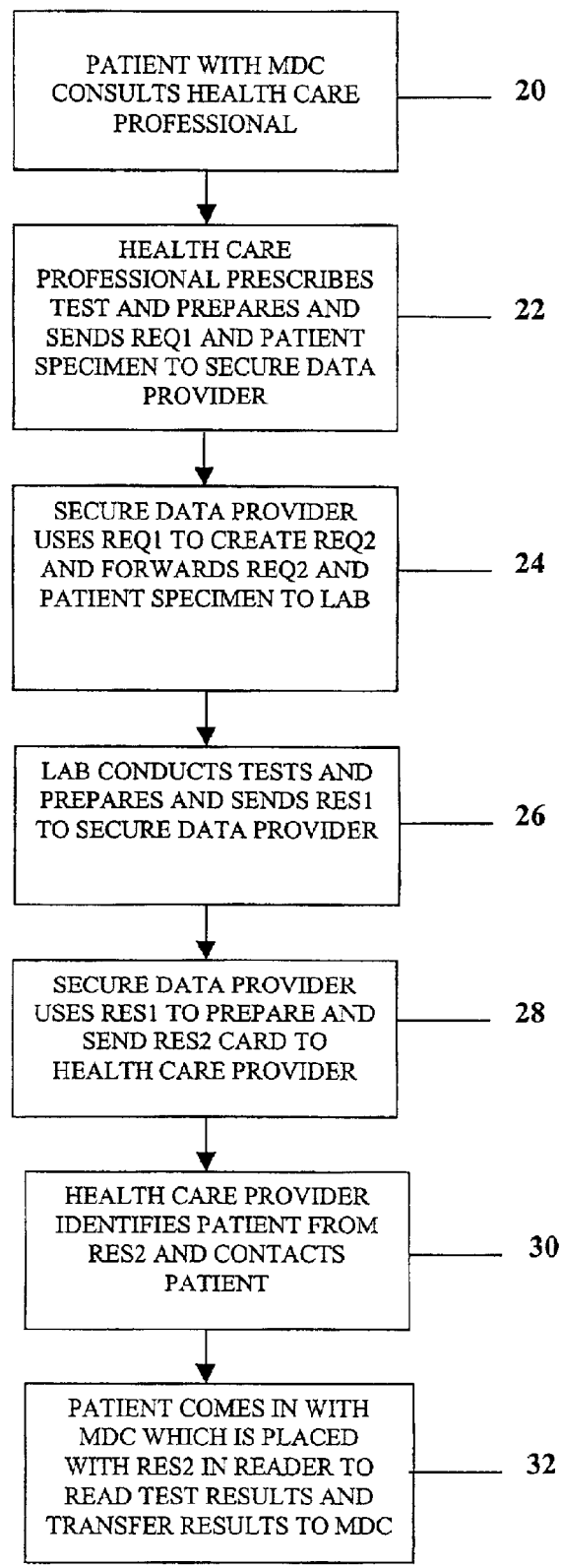
FIG. 1 is a flow chart of a method of privately and securely reporting medical tests results according to the principles of this invention.
Figure 2:
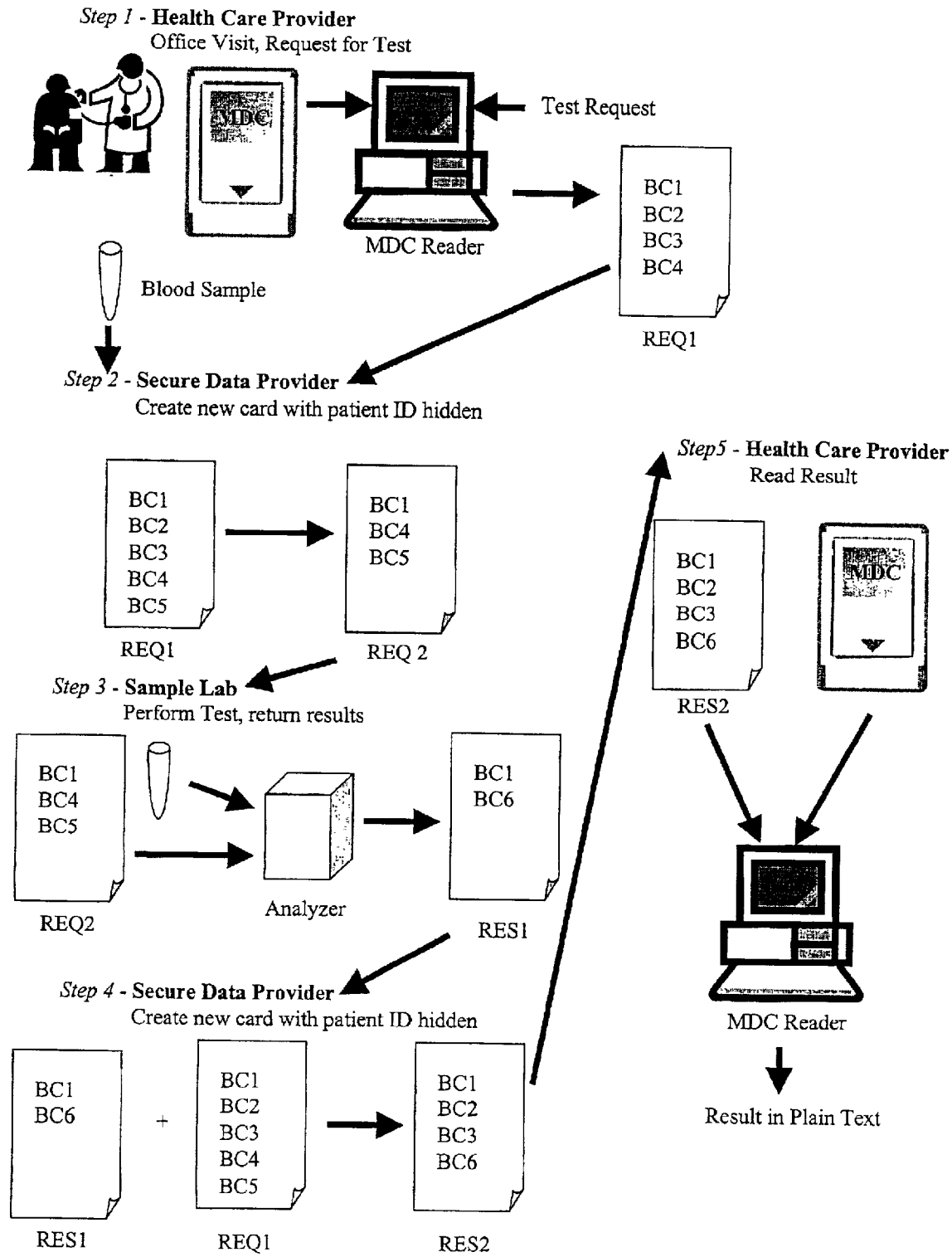
FIG. 2 is a schematic view of the method shown in FIG. 1.
Figure 3:
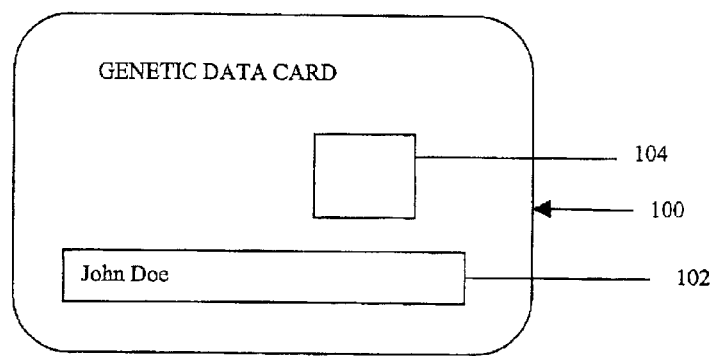
FIG. 3 is a plan view of a medical data card constructed according to the principles of this invention, for use with the method of this invention.

The present invention includes both methods and apparatus for ensuring the privacy and security of personal medical information, including but not limited to genetic testing information. A flow chart of the method of the present invention is shown in FIG. 1, and the method is shown schematically in FIG. 2. In accordance with the preferred embodiment of this invention, a patient would apply to a secure data provider for a medical data card, and would be issued a card. As shown in FIG. 3 and described herein, the MDC 100 is adapted for use in facilitating genetic testing for a predicted clinical outcome, such as susceptibility to disease and/or response to a particular drug therapy. However, the invention is not so limited, and thus, the medical data card could be adapted for other types of medical testing or adapted for both genetic and other medical testing.

The MDC 100 is preferably compact, for example the size of a standard credit card (about 3.4 inches by about 2.1 inches) so that the patient could conveniently carry the card with him or her in a wallet or purse with other medical cards, such as insurance cards. The MDC 100 preferably has identifying indicia 102, such as the patient's name, imprinted or embossed thereon, so that the patient can correctly identify his or her card. The MDC 100 may also include information (not shown), such as the name, address, telephone number, or other contact information about the issuing secure data provider. The MDC 100 preferably also includes a data storage element 104. The data storage element 104 is readable, and preferably both readable and writeable. The data storage element 104 may be, for example, a magnetic stripe or other magnetic media on the card; an embedded memory chip or other electronic storage media, an optically readable and writeable media, or any other suitable element for storing data. In the preferred embodiment, the data storage element 104 is a computer readable and writeable memory chip.

Stored in the memory of the chip of the data storage element 104 is information about the patient and about the tests that have been conducted. In the preferred embodiment this information would include the information shown in Table 1 below:

TABLE 1

Information on the MDC

| Field Name | Description |
|---|---|
| PID | Unique patient ID |
| Test Type | Type of the current test |
| Test ID | Unique ID for that test for that patient |
| Results | Results of the test - usually a short string of characters of a yes/nor or a +/- |
| Key 1 | Public key encryption private key |
| Key 2 | Public key encryption public key |

As is apparent from the Table 1, in the preferred embodiment the MDC 100 contains a single unique patient identification code (PID), a single unique public key encryption private key (Key 1), and a single unique public encryption public key (Key 2). The MDC 100 is also capable of storing data relating to one or more tests. The data for each test preferably includes data on the test type, a unique identification number or code (ID) for the lest, and the results of the test.

Figure 4:
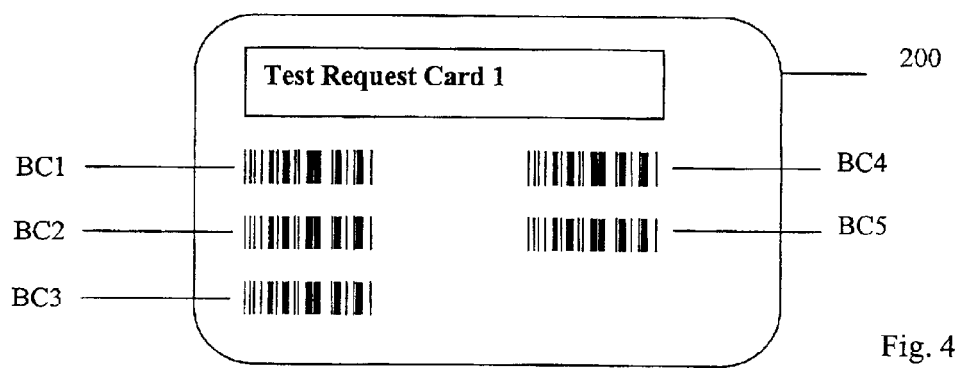
FIG. 4 is a plan view of a first test request card constructed according to the principles of this invention, for use with the method of this invention.

As shown in FIG. 1, at 20 a patient with a MDC 100 consults a health care provider, for example a hospital, a clinic, or a private physician's office. As shown in FIG. 1, at 22 if the health care provider prescribes a medical test, such as a genetic test, the health care provider takes the appropriate specimen (e.g., a blood specimen) from the patient, and uses the patient's MDC 100 to prepare a first test request card (REQ1) 200. See FIG. 4. The REQ1 200 will preferably include the information in Table 2 in bar code (BC) format:

TABLE 2

Information on the REQ1

| Field Name | Description |
|---|---|
| BC1 | An encrypted concatenation of the PID, the Test Type and the Test ID |
| BC2 | A code corresponding to the particular health care provider prescribing the test |
| BC3 | The PID |
| BC4 | Key 2 (the public encryption public key) |
| BC5 | Test type |

The information provided on the REQ1 200 can be stored in any convenient manner, including optically, magnetically, or electrically. In the preferred embodiment the information is printed on the card in bar code form, which is easy to print and easy to read with readily available, relatively inexpensive equipment. The REQ1 could be in the form of a label applied to the container of the specimen, for example on a vial, or on a bag containing the vial, so that the REQ1 can be removed and replaced by the secure data provider as explained below. BC1 is a combination or concatenation of the PID read from the patient's MDC, the test type entered by the health care provider, and a unique test identification number. This number can either be obtained from the secure information provider, or generated by the hardware/software provided by the secure information provider. This combination or concatenation is encrypted using the Key 2 read from the patient's MDC. The BC1 is a unique identifier for this patient-test combination. BC2 is an identification code for the health care provider. This can be an identification code assigned by the secure information provider, or an identification code assigned by some third party, that uniquely identifies the health care provider. BC3 is simply the PED obtained from the patient's MDC. BC4 is the Key 2 obtained from the patient's MDC. BC5 is simply an identification of the type of test prescribed by the health care provider. The REQ1 200 will also have, in plain text, the address of the secure data provider.

Figure 5:
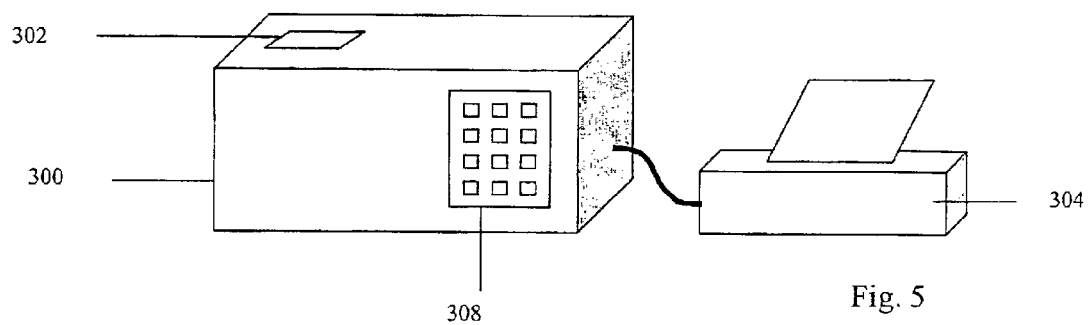
FIG. 5 is a schematic diagram of a reader for reading medical data cards and printing test request cards for use with the method of this invention.

At the time that a health care provider prescribes a particular test, and in this preferred embodiment a genetic test, the patient inserts his or her MDC 100 into a reader unit 300 (shown in FIG. 5). The reader unit 300 has a slot 302 into which the MDC 100 can be inserted, to read the data storage in element 104. The reader unit 300 also includes a printer 304 for printing the REQ1 200.

Figure 6:
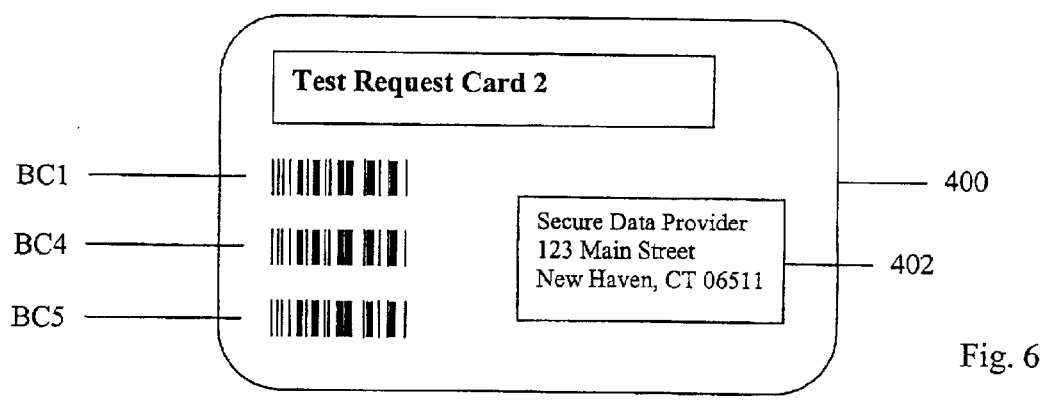
FIG. 6 is a plan view of a second test request card constructed according to the principles of this invention, for use with the method of this invention.

As shown in FIG. 1, at 24, the secure data provider receives the REQ1 200 and the accompanying specimen, and prepares a second test request card (REQ2) 400 that is devoid of any accessible identification of the patient. See FIG. 6. The REQ2 can be in the form of a label that is attached to the container for the specimen, for example a vial, or it can be attached to a bag containing the vial. More specifically, the REQ2 400 includes only BC1, BC4, and BC5 and the address of the secure data provider 402. The secure data provider sends the specimen and the REQ2 400 to a laboratory which conducts the prescribed tests. These can be sent in a plain envelope, so there is nothing on the package to indicate the identity of the patient. BC1 is a unique identifier of the sample, but because it is encrypted the laboratory cannot determine the identity of the patient.

Figure 7:
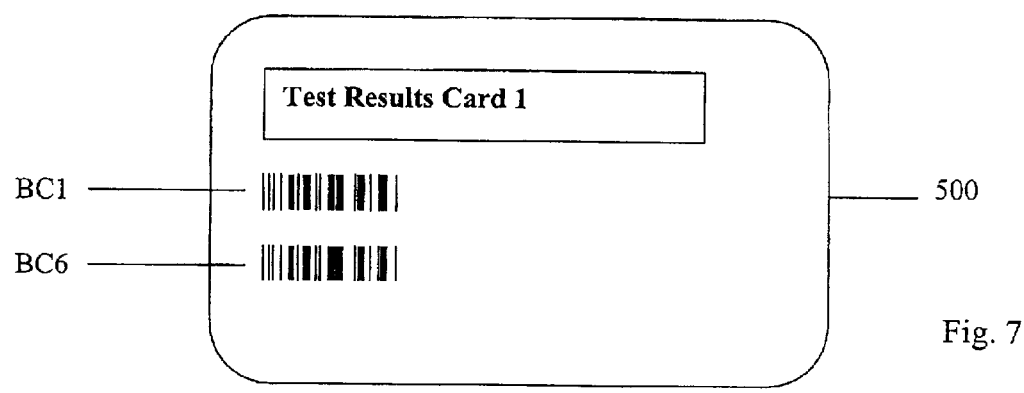
FIG. 7 is a plan view of a first test results card constructed according to the principles of this invention, for use with the method of this invention.
Figure 8:
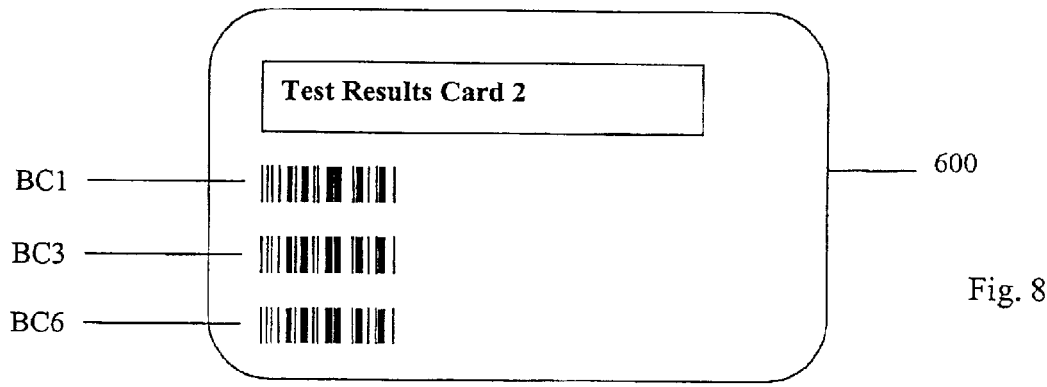
FIG. 8 is a plan view of a second test results card constructed according to the principles of this invention, for use with the method of this.
Figure 9:
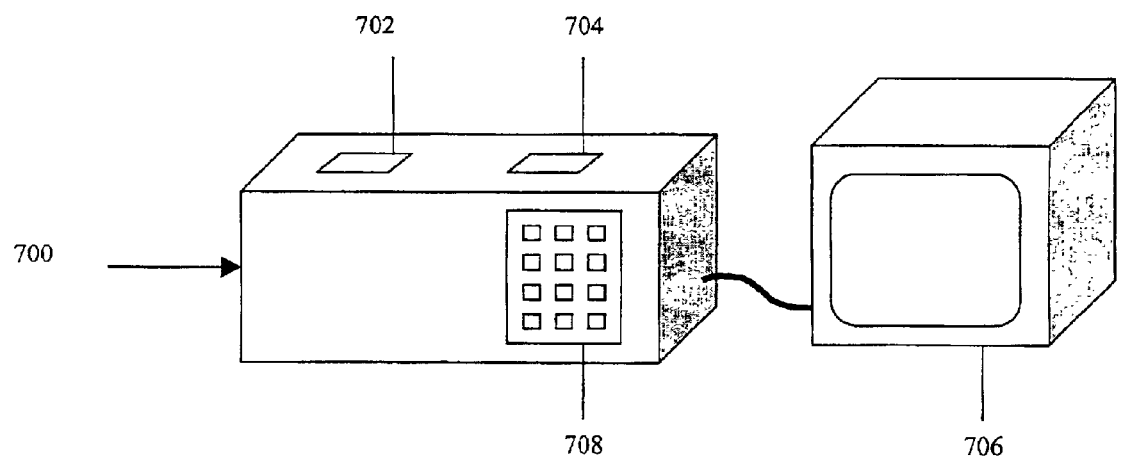
FIG. 9 is a schematic view of a reader for reading test results cards and displaying the results, for use with the method of this invention.

As shown in FIG. 1, at 26, the laboratory then performs the prescribed test (identified to the laboratory in BC5 on the REQ2 400), and encrypts the results (using BC4 on the REQ2 400). The encrypted results are recorded as another bar code, BC6. The laboratory prepares a first test results card (RES1) 500. See FIG. 7. The RES1 500 contains specimen-identifying information (BC1, which is encrypted, from the REQ2 400) and the results (BC6, which is also encrypted), and sends the RES1 500 to the secure data provider, identified at 402 on the REQ2 400.

As shown in FIG. 1, at 28, the secure data provider receives the RES1 500, and identifies the health care provider (BC2) and the patient identifier PIC (BC3) corresponding to the BC1 on the RES1 500. The secure data provider then prepares a second test results card (RES2) 600 containing BC1, BC3, and BC6, and sends the RES2 600 to the health care provider.

As shown in FIG. 1, at 30, the health care provider receives the RES2 600, and using the PID (BC3) on the RES2, looks up the patient contact information, and requests that the patient come in. The patient comes in and brings his/her MDC 100. The patient's MDC 100 is inserted into a reader 700 along with the RES2 600. The reader takes the private key (Key 1) from the MDC 100, decrypts BC1 (to identify the test) and decrypts BC6 (the results). The results of the test is then written to the MDC 100 and displayed on a display for the health care provider's use. The health care provider then makes his or her diagnostic or therapeutic treatment decision based on these results. The decision can be recorded in the patient's permanent record, but the actual test results are not. After the data is transferred from the RES2 600 to the patient's MDC 100, the RES2 600 is erased and discarded, leaving the MDC as the only permanent record of the test results, with a backup at the secure data provider.

In the preferred embodiment, a reader 700 is provided for reading the RES2 600. The reader 700 has two slots 702 and 704 for receiving the MDC 100 and the RES2 600, and a display 706 for displaying the test results. The use of a reader 700 ensures that the patient does not access the test results without proper supervision or explanation from a health care provider.

In the preferred embodiment, after the results are read on the display 706, the information is transferred from the RES2 600 to the storage element 104 of the MDC 100, so that the patient has a record of the information for future use and reference, but there is no other record of the results available that is identified specifically with the patient. The health care professional can then determine a proper course of action based upon the genetic testing results.

Of course, access to the data storage element 104 of the MDC 100 can be protected with a PIN (personal identification number) so that mere access to the MDC 100 alone will not allow access to either the patient's unique identification number and/or to the information stored in the MDC. In this case the readers 300 and 700 would also include keypads 308 and 708, respectively, so that the patient can enter his or her PIN to enable the reader 300 to read the patient's unique PID, or to allow the reader 700 to read the MDC 100 containing the patient's test results. For convenience the reader 300 and the reader 700 could be consolidated into one device.

OPERATION

A patient applies for and obtains a MDC 100. As illustrated in FIG. 2, at some point a health care provider prescribes a particular genetic test, or other medical test. The patient inserts his or her MDC 100 into the slot 302 of the health care providers reader 300, keys in his or her PIN, and a REQ1 200 is printed. The health care provider takes the appropriate specimen, for example a blood specimen, and sends the specimen with the REQ1 400 to the secure data provider. The secure data provider prepares a REQ2 400 and forwards the specimen the REQ2 to a laboratory. The laboratory conducts the tests identified on the REQ2 400, and prepares a report RES1 500, and sends the RES1 to the secure data provider. The secure data provider prepares a RES2 600, and forwards it to the health care provider. The patient inserts the MDC 100 into slot 702 of the reader 700, and the RES2 600 into the slot 704 of the reader. The patient keys in his or her PIN on the keypad 708, and the reader 700 decodes the test results stored on the RES2 and displays them on display 806. The reader preferably also transfers the information from the RES2 600 to the element 104 on the MDC 100, so that the patient has a record of the test results. If the information is needed in the future, the patient can bring the MDC to the health care institution, insert it into a reader 700, enter his or her PIN, and access the results of the prior tests. If the MDC 100 is lost or stolen, a duplicate can be assembled from the records maintained by the secure data provider.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of ensuring the security of a patient's results from a medical test conducted by a laboratory, the method comprising:

providing the patient with a medical data card containing a unique patient identification number;

taking a specimen from the patient for conducting the medical test;

generating a first medical test request containing the unique patient identification number using the patient's medical data card; and transmitting the specimen and the first medical test request to a secure data provider, wherein the secure data provider generates a second medical test request devoid of publicly accessible patient identification information using the first medical test request, transmits the specimen and the second medical test request to the laboratory, receives the results from the medical test from the laboratory, and reports the results on a test results card that can only be read in conjunction with the patient's medical data card.

2. The method according to claim 1 wherein the patient's medical data card includes a memory, and further comprising the step of storing the results in the memory on the patient's medical data card.

3. The method according to claim 1 wherein the patient identification number is not readable from the patient's medical data card without a PIN, and wherein the step of generating the first medical test request includes the patient supplying the PIN.

4. The method according to claim 1 further comprising reading the results on the test results card using the patient's medical data card.

5. The method according to claim 4 wherein the results are not readable with the medical data card without a PIN, and wherein the step of reading the results on the test results card includes the patient supplying the PIN.

6. A method of ensuring the security of a patient's results from a medical test conducted for a medical provider by a laboratory, the method comprising:

issuing the patient a medical data card containing a unique patient identification number;

receiving from the medical provider a first medical test request generated using the patient's medical data card and a patient specimen for use in conducting the medical test;

generating a second medical test request using the first medical test request, the second medical test request being devoid of publicly accessible information about the identity of the patient;

forwarding the second medical test request and the specimen to the laboratory for conducting the medical test;

receiving the results of the medical test from the laboratory; and providing the results to the medical provider in a form that can only be read in conjunction with the patient's medical data card.

7. The method of claim 6, wherein the results are on a test results card in computer readable form and the method further comprises providing the medical provider with a reader adapted for reading the tests results.

8. A method of ensuring the security of a patient's results from a medical test conducted for a medical provider by a laboratory, the method comprising:

issuing the patient a medical data card containing a unique patient identification number;

receiving from a medical provider a first medical test request generated using the patient's medical data card and a patient specimen for use in conducting the medical test;

generating a second medical test request using the first medical test request, the second medical test request having encrypted information identifying the patient but being devoid of publicly accessible information about the identity of the patient, and including a public encryption public code specific to the patient;

forwarding the medical test second request and the specimen to the laboratory for conducting the medical test;

receiving the results of the medical test from the laboratory, wherein the results are encrypted using the public encryption public code on the second medical test requests;

identifying the patient to whom the results pertain; and providing the encrypted results to the medical provider, wherein the encrypted results can only be decrypted to conjunction with the patient's medical data card.

9. A method of ensuring the security of a patient's results from a medical test conducted for a medical provider by a laboratory, comprising:

providing the patient with a medical data card issued by a secure information provider, having a unique patient identification number, a public key encryption private key, and a public key encryption public key;

taking a specimen from the patient for conducting the medical test;

generating a first medical test request using the patient's medical data card, the first medical test request including an encrypted identification of the patient and the medical test; 'a code identifying the medical provider; the patient identification number; the public encryption public key; and an identification of a medical test type;

forwarding the first medical test request and the specimen to the secure information provider;

generating a second medical test request including an encryption of the patient's unique patient identification number, but otherwise devoid of any indicia that would identify the patient, and an encryption code;

forwarding the second medical test request and the specimen to the laboratory, wherein the laboratory conducts the medical test and provides the results of the medical test in encrypted form using the encryption code on the second medical test request;

receiving the encrypted results;

identifying the medical provider from encrypted information included with the encrypted results;

forwarding the encrypted results to the medical provider with an identification of the patient; and decrypting the encrypted results using the patient's medical data card.

* * * * *